(12) United States Patent
Webster et al.

(10) Patent No.: US 8,115,922 B2
(45) Date of Patent: Feb. 14, 2012

(54) APPARATUS AND METHOD FOR ADAPTING CONVENTIONAL CUVETTES FOR USE IN A VERTICAL LIGHT BEAM SPECTROPHOTOMETER

(75) Inventors: John Russell Webster, Atascadero, CA (US); Alan Keith Hulme, Hainault (GB)

(73) Assignee: Starna Cells, Inc., Atascadero, CA (US)

( * ) Notice: Subject to any disclaimer, the term of this patent is extended or adjusted under 35 U.S.C. 154(b) by 757 days.

(21) Appl. No.: 12/040,117

(22) Filed: Feb. 29, 2008

(65) Prior Publication Data

US 2009/0219527 A1 Sep. 3, 2009

(51) Int. Cl.
*G01J 3/42* (2006.01)
*G01N 21/01* (2006.01)
*G01N 1/10* (2006.01)
*G01N 21/00* (2006.01)
*G01N 21/75* (2006.01)
*C12M 1/34* (2006.01)
*C12M 3/00* (2006.01)

(52) U.S. Cl. ........ 356/319; 356/244; 356/246; 356/432; 422/82.05; 422/82.09; 435/288.7; 436/164

(58) Field of Classification Search .................. None
See application file for complete search history.

(56) References Cited

U.S. PATENT DOCUMENTS

| 3,441,352 A | * | 4/1969 | Hughes | 356/419 |
| 3,531,211 A | * | 9/1970 | Staunton | 356/244 |
| 4,123,173 A | * | 10/1978 | Bullock et al. | 356/246 |
| 4,290,997 A | * | 9/1981 | Suovaniemi | 422/73 |
| 4,652,137 A | | 3/1987 | Calzi | |
| 4,682,890 A | * | 7/1987 | de Macario et al. | 356/244 |
| 4,764,342 A | * | 8/1988 | Kelln et al. | 422/72 |
| 5,048,957 A | | 9/1991 | Berthold | |
| 5,216,488 A | | 6/1993 | Tguunanen | |
| 5,250,440 A | * | 10/1993 | Kelln et al. | 436/48 |
| 5,258,308 A | | 11/1993 | Freeman et al. | |
| 5,567,617 A | | 10/1996 | Caprio et al. | |
| 5,628,428 A | * | 5/1997 | Calhoun et al. | 221/197 |
| 5,774,209 A | | 6/1998 | Shestock | |
| 5,963,318 A | | 10/1999 | Held | |
| 6,074,614 A | | 6/2000 | Hafeman et al. | |
| 6,074,615 A | * | 6/2000 | Lewis et al. | 422/547 |

(Continued)

FOREIGN PATENT DOCUMENTS

GB  1 486 210  9/1977

(Continued)

OTHER PUBLICATIONS

Thermo Fisher Scientific Part # 402237, Holmium perchlorate filter for insertion in filter wheel; First sale date in USA; Dec. 29, 1995.

(Continued)

*Primary Examiner* — Tarifur Chowdhury
*Assistant Examiner* — Gordon Stock, Jr.
(74) *Attorney, Agent, or Firm* — Eleanor M. Yost; Goodwin Procter LLP (57) ABSTRACT

The invention relates to an apparatus and method for adapting conventional spectrophotometer cuvettes for use in a vertical light beam spectrophotometer.

28 Claims, 7 Drawing Sheets

U.S. PATENT DOCUMENTS

| | | | |
|---|---|---|---|
| 6,198,536 | B1 | 3/2001 | Baker |
| 6,238,625 | B1* | 5/2001 | Chang et al. ............... 422/82.09 |
| 6,339,472 | B1 | 1/2002 | Hafeman et al. |
| 6,340,589 | B1 | 1/2002 | Turner |
| 7,061,608 | B2 | 6/2006 | Bradshaw et al. |
| 2002/0155619 | A1 | 10/2002 | Kurihara |
| 2003/0107738 | A1 | 6/2003 | Curtis |
| 2004/0246501 | A1* | 12/2004 | Curtis ........................... 356/627 |
| 2005/0168737 | A1* | 8/2005 | Bradshaw et al. ............ 356/319 |

FOREIGN PATENT DOCUMENTS

| WO | WO-2008/044037 | 4/2008 |
|---|---|---|

OTHER PUBLICATIONS

Thermo Fisher Scientific Part # 420104, Potassium Dichromate filters for insertion in filter wheel; First sale date in USA; Oct. 1, 1997.

Drawings and photographs of cells shown at PITTCON tradeshow in 2002, 9 pages.

International Search Report dated Jul. 20, 2008 in corresponding Application No. PCT/US08/55561.

UV/Vis Photodiode Array Detector, www.chromtech.com, p. 228, 1 page.

Email dated May 16, 2007 regarding May 2007 sale of cuvettes designed to be used with a horizontal plate reader to Artel, 4 pages.

* cited by examiner

APPARATUS AND METHOD FOR ADAPTING CONVENTIONAL CUVETTES FOR USE IN A VERTICAL LIGHT BEAM SPECTROPHOTOMETER

FIELD OF THE INVENTION

This invention relates to an apparatus and method for adapting conventional spectrophotometer cuvettes for use in a vertical light beam spectrophotometer.

BACKGROUND OF THE INVENTION

Spectrophotometers are laboratory tools for analyzing or testing liquid samples of, for example, chemical solutions or mixtures, biologic materials, biochemical materials, biochemical reactions, and the like. Typically, two types of spectrophotometers are available: the vertical light beam spectrophotometer, in which the analyzing light beam is transmitted in the vertical direction through a sample disposed in a horizontal plane; and the horizontal light beam spectrophotometer in which the analyzing beam is transmitted in the horizontal direction through a sample disposed in a vertical plane.

Most conventional spectrophotometers employ a horizontal light beam that traverses the liquid sample horizontally so as to avoid passing through the liquid-gas interface that is typically above the sample. With such horizontal light beam photometers, the geometry and optical pathlength within the sample is fixed for any given cuvette. For visible and ultraviolet light absorption measurements, for example, cuvettes customarily have a 1 cm pathlength. Cuvettes with pathlengths between 0.1 cm and 10 cm are also common, however.

Vertical light beam spectrophotometers also measure light absorption. In vertical light beam spectrophotometers, however, the light beam typically passes only through one wall of the sample-retaining device, through the sample, and through the interface between the sample a surrounding gas atmosphere (which is usually air).

The latter liquid-gas interface, the meniscus, is usually curved. The specific shape of the meniscus depends upon the interactions between the liquid sample and the gas and the sidewalls of the sample-retaining device. Depending upon the design of a particular vertical light beam spectrophotometer the light beam may traverse the meniscus either before or alter passing through the sample. In either case, the optical pathlength through the sample is not a constant value. Instead, the optical pathlength is related to the sample volume and the meniscus shape. The nature of the sample, the sample-retaining device surfaces, and the gas each contributes to the shape of the meniscus, quantitatively affecting the optical pathlength through the sample.

Vertical light beam spectrophotometry has become a popular technique, despite the disadvantage of not having a fixed optical pathlength through the sample. This popularity stems from the fact that the optical characteristics of multiple samples may be analyzed with a vertical-beam photometer in a small period of time. Typically, vertical light beam spectrophotometers monitor the optical characteristics of samples disposed in the wells of, for example, 96-well multi-assay plates. The optical characteristics, such as light absorption or light scattering, of the samples contained within each well of such multi-assay plates may be monitored in a few seconds. Vertical light beam spectrophotometers also allow repetitive measurements of multiple samples to be made with short intervals between each of a series of measurements.

The use of vertical light beam spectrophotometers in clinical assays is therefore important. These vertical light beam spectrophotometers are calibrated, and the calibrations are verified by the manufacturer. However, it is both necessary and good practice to routinely validate the performance of these instruments in the course of clinical practice, and may in fact be required by regulatory agencies overseeing such practice.

There exists a number of U.S. patents directed to verifying the calibration of vertical light beam spectrophotometers, including U.S. Pat. No. 5,258,308 issued to Freeman, et. al., entitled "Method, kit and apparatus for verifying calibration and linearity of vertical photometers," ("Freeman"). Freeman describes a method and means of verifying the calibration of vertical light beam spectrophotometers comprising pre-dispensed dye check strips which provide reproducible standards by which the functioning of the spectrophotometer can be ascertained. Each strip contains a plurality of microtiter wells containing a dried dye material which when reconstituted can be read in the various models of photometers and spectrophotometers to assess instrument performance.

U.S. Pat. No. 5,963,318 issued to Held, entitled "Method of and apparatus for performing fixed pathlength vertical photometry," ("Held") describes a system for performing vertical light beam spectrophotometric determinations using a vessel which has an upper transparent surface and a lower transparent surface which are spaced apart to define a known fixed pathlength through which a light beam is transmitted. The vessel also includes a portion disposed above the upper surface which may be a spout having an opening for allowing the introduction of substances into the containment portion.

Like Held, U.S. Pat. No. 6,074,614 issued to Hafeman, et. al., entitled "Multi-assay plate cover for elimination of meniscus." ("Hafeman") also describes a vessel having a constant pathlength, where the vessel comprises a flat top side and a flat bottom side, the bottom side having solid cylindrical projections of equal length extending downwardly from the flat bottom side, wherein each cylindrical projection is centered about the optical axis passing through a corresponding sample well of a multi-assay plate, thereby eliminating meniscus and evaporation effects.

Freeman, Held, and Hafeman each describe a specialized vessel designed exclusively for calibrating and validating a vertical light beam spectrophotometer. They illustrate how a user is limited to specialized cuvettes when using a vertical light beam spectrophotometer. Accordingly, there is a need in the art for a device and method for using, calibrating, and validating a vertical light beam spectrophotometer using conventional cuvettes.

Others have attempted to validate vertical light beam spectrophotometers with conventional cuvettes in the past. For example, as discussed in U.S. Pat. No. 7,061,608 to Bradshaw. et. al., one method for calibrating vertical light beam spectrophotometers involves the testing of reference cuvettes having samples of reference concentrations. Solutions containing different concentrations of the specific dye are first sealed in conventional cuvette. Such "reference samples" or "reference solutions" typically have a known or expected absorbance measurement for comparison by a user to a measurement obtained from the spectrophotometer to be validated. However, this general method has limitations that constrain its usefulness. Bradshaw, et. al. points out that sealed cuvettes require an expansion allowance zone including a compressible component that may be a bubble of gas (such as air) to allow for the solution to expand/contract due to thermal fluctuations. This compressible component must be held out of the light beam path when such cuvettes are placed horizontally in a vertical light beam spectrometer, or it will adversely affect the absorbance values measured. Bradshaw, et. al. discloses an enclosed calibration plate including one or more sealed reference cuvettes having specialized bubble traps used to hold the compressible component in place in the expansion allowance zone, out of the beam path near the top of the cuvette. However, an easy to use system that does not require the use of specialized cuvettes having, e.g., bubble traps is still needed.

Accordingly, the present invention is directed an adaptor plate to allow the use of conventional spectrophotometer cuvettes with a vertical light beam spectrophotometer without the need for specialized cuvettes, or bubble traps, as discussed above.

SUMMARY OF THE INVENTION

The invention comprises, in one form thereof, an apparatus for use in a vertical light beam spectrophotometer comprising: a plate having a top face, a bottom face, and one or more openings for passage of light through the plate; wherein at least a portion of the top face is configured such that an end of at least one cuvette aligned over one or more of the openings in the top face is propped in a vertical direction relative to the opposite end of the cuvette. In some embodiments, this apparatus can replace a conventional cuvette support that is normally used with the spectrophotometer.

More particularly the invention includes an apparatus for use in a vertical light beam spectrophotometer comprising: a plate having a top face, a bottom face, and one or more openings for passage of light through the plate; wherein at least a portion of the top face is configured such that a first end of at least one cuvette is aligned over one or more of the openings in the top face by one or more aligning walls, and a second end of the at least one cuvette is propped in a vertical direction relative to the first end of the cuvette by a raised element.

In another form, the invention includes a method for adapting conventional cuvettes for use in a vertical light beam spectrophotometer. The method comprises the steps of: providing at least one cuvette with a first end and a second end opposite the first end; providing an adaptor plate having: (a) a top face, (b) a bottom face, and (c) one or more openings for passage of light through the plate wherein at least a portion of the top face is configured such that the first end of at least one cuvette is propped in a vertical direction relative to the opposite end of the cuvette; aligning the cuvette over the one or more openings, such that light passes through the cuvette; and using the vertical spectrophotometer to obtain a reading for a sample in the cuvette.

In another form, the present invention permits use of reference cuvettes traditionally used in horizontal light beam spectrophotometers in vertical light beam spectrophotometers. One anticipated commercial advantage of the invention is that a customer can use the same reference cells in both horizontal and vertical light beam spectrophotometers using only the present invention. The customer thus saves the cost of purchasing additional reference cells specially designed for vertical light beam spectrophotometers.

More specifically, the present invention is directed to a method of calibrating or validating a vertical light beam spectrophotometer comprising the steps of: providing at least one cuvette with a first end and a second end opposite the first end and containing a reference sample: providing an adaptor plate having: (a) a top face, (b) a bottom face, and (c) one or more openings for passage of light through the plate, wherein at least a portion of the top face is configured such that the first end of the cuvette is propped in a vertical direction relative to the opposite end of the cuvette; aligning the cuvette over the one or more openings, such that light is able to pass through the cuvette; operating the vertical spectrophotometer to obtain a reading or measurement for the reference sample; and validating that the vertical spectrometer is performing within acceptable tolerance limits by comparing the obtained reading or measurement with the reference sample's known measurement value.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

In short, the typical sequence of events in a spectrophotometer analysis is as follows: (1) a sample (held in a cuvette) is disposed in the spectrophotometer; (2) a light source shines through the cuvette and sample, and the sample absorbs light; (3) a detector detects how much light the sample has absorbed; (4) the detector then converts how much light the sample absorbed into a number or signal; and (6) the number or signal is displayed, plotted or transmitted to a computer to be further manipulated (e.g. curve smoothing, baseline correction, comparison to a reference etc.). Herein, the number or signal is referred to as a reading or measurement.

Figure 1:
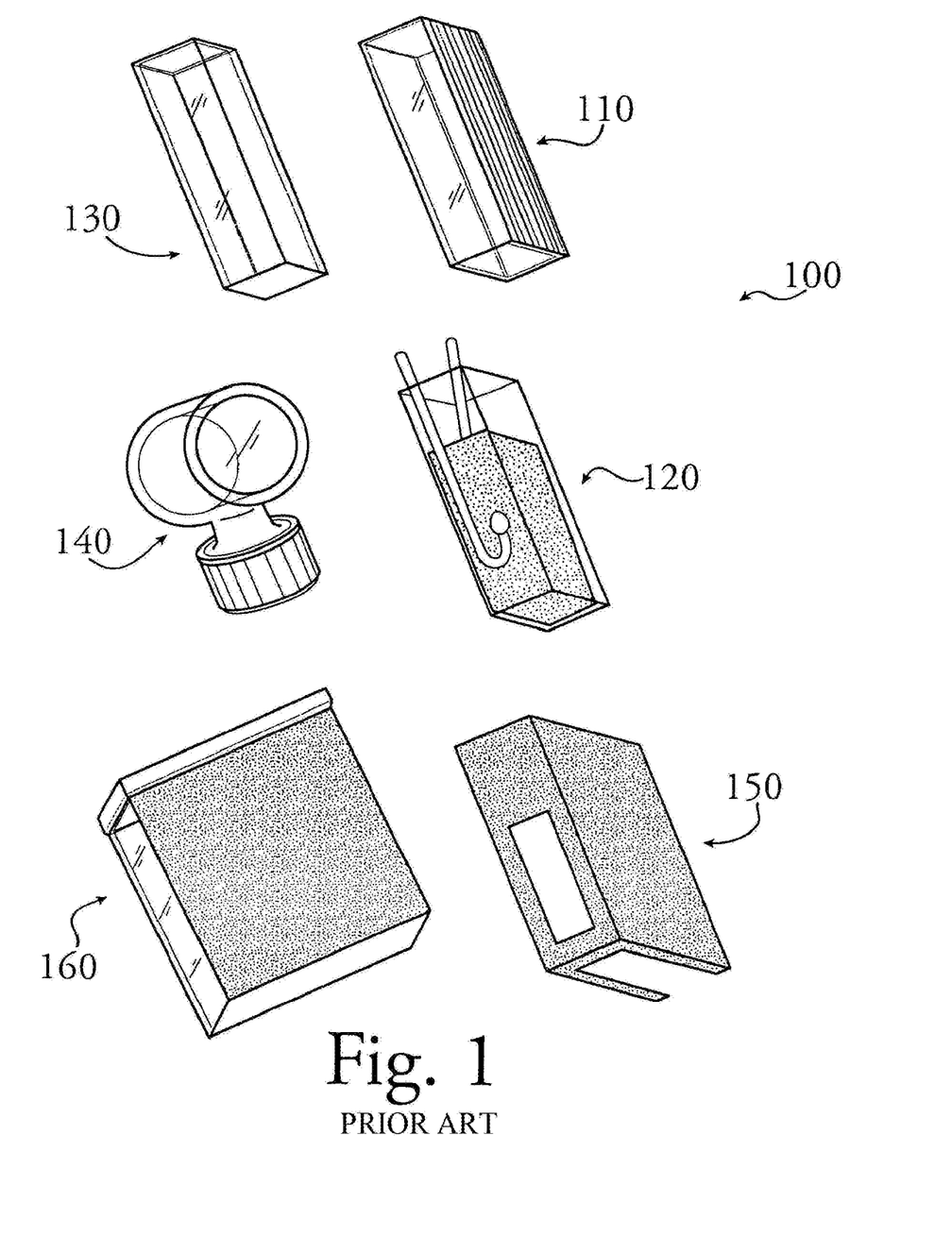
FIG. 1 is an illustrative view of exemplary conventional cuvettes.

FIG. 1 shows illustrations of a variety of conventional cuvettes 100; cuvettes are also referred to herein as spectrophotometer cells or simply as cells. Typically, cuvettes as shown in FIG. 1 are used in connection with horizontal light beam spectrophotometers. A cuvette is a kind of laboratory glassware, usually a small tube of circular or square cross-section made of plastic, glass, or optical grade quartz, and designed to hold samples for spectroscopic experiments and may be sealed on at least one end. Disposable plastic cuvettes, while not as optically clear as glass or quartz versions, are often used in fast spectroscopic assays, where speed is more important than high accuracy. Typically, the best cuvettes are as clear as possible, without impurities that might affect a spectroscopic reading. Like a test tube, a cuvette may be open to the atmosphere on top or have a glass or plastic cap to seal it shut. Parafilm or the like can also be used to seal a cuvette. Reference cuvettes may be permanently heat sealed. Conventional cuvettes are round, square, or rectangular and may look similar to test tubes. Typically, cuvettes are about one centimeter across to allow for easy calculations of co-efficients of absorption. The cuvettes are used for holding samples to be measured for absorbance or transmission in common spectrophotometers. As known to those skilled in the art, there are accepted international standards for the size, shape and materials for the construction of cuvettes.

Some cuvettes 110 will be clear only on opposite sides, so that they pass a single beam of light through that pair of sides; often the unclear sides have ridges or are rough to allow easy handling. Cuvettes to be used in fluorescence spectroscopy are typically clear on all four sides. Some cuvettes, known as tandem cuvettes, have a glass barrier that extends approximately two-thirds up inside the cuvette, so that measurements can be taken with two solutions separated, and again when they are mixed. Flow cells 120 are frequently used for measuring samples with continuous flow as in chromatography or on-line production monitoring such as tablet dissolution. They may also be used in sipper systems where individual samples are aspirated into and out of the cell either by a syringe or pumping system. A wide variety of flow cell designs are available because different applications require the optimization of sample availability, by sample volume constraints; beam geometry; flow characteristics and path length. Instruments also have differing tube connection requirements relating to the pumping system used.

Examples of other conventional cuvette types include: cylindrical 140; glass or quartz filters 150; wide 160; semi-micro; micro; sub-micro; screw cap; flow through; micro flow; water jacketed; fluid filled reference; anaerobic thumbert; tandem; demountable; cryogenic; quartz to pyrex graded seal; etc.

Rectangular cells 130 are used for most routine analyses. By far the most common type of cell, they have at least two clear windows and conform to international standard dimensions. Typically, such cells have a 10 mm (1 cm) pathlength size to fit most instruments that use rectangular cells.

In vertical light beam spectroscopy, a number of diagnostic assays are typically carried out in equipment using multiwell plastic plates and equipment in which a vertical beam of light is used in making spectrophotometric readings in the individual wells of the plates. These plates generally have several common features, namely, plastic wells with optically transparent bottoms are isolated from one another with respect to liquid contained therein, but physically connected in a precise geometric pattern. The wells are typically part of a plastic carrier plate, and the automated equipment is designed to have a movable stage into which one or more multiwell plates precisely fit. Most commonly these multiwell plates contain 96 wells arranged in an 8 times 12 pattern, although plates containing other numbers of wells are also available.

In some instances, however, a user may desire to perform an analysis of a single sample in a vertical light beam spectrophotometer, and thus, a conventional 96, 384, or 1536 multiwell plate may be undesirable; using a multiwell plate for a single or few samples would be wasteful. Similarly, a user may desire to perform an analysis of a number of samples in a vertical light beam spectrophotometer where the number is significantly smaller than the available wells in a typical multiwell plate. One embodiment of the present invention provides an adaptor for a vertical light beam spectrophotometer for analyzing samples contained in conventional cuvettes.

Figure 2:
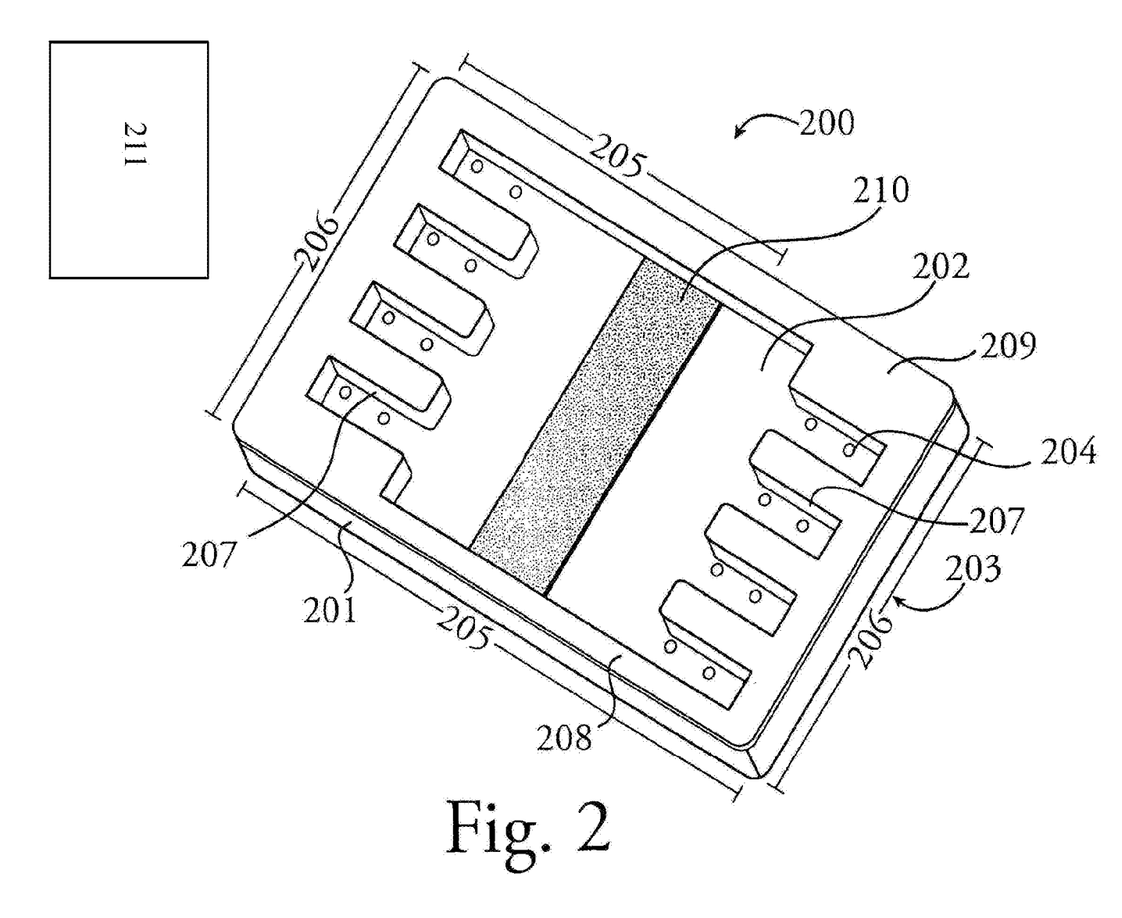
FIG. 2 is a view of a first embodiment of the adaptor plate of the present invention.
Figure 3:
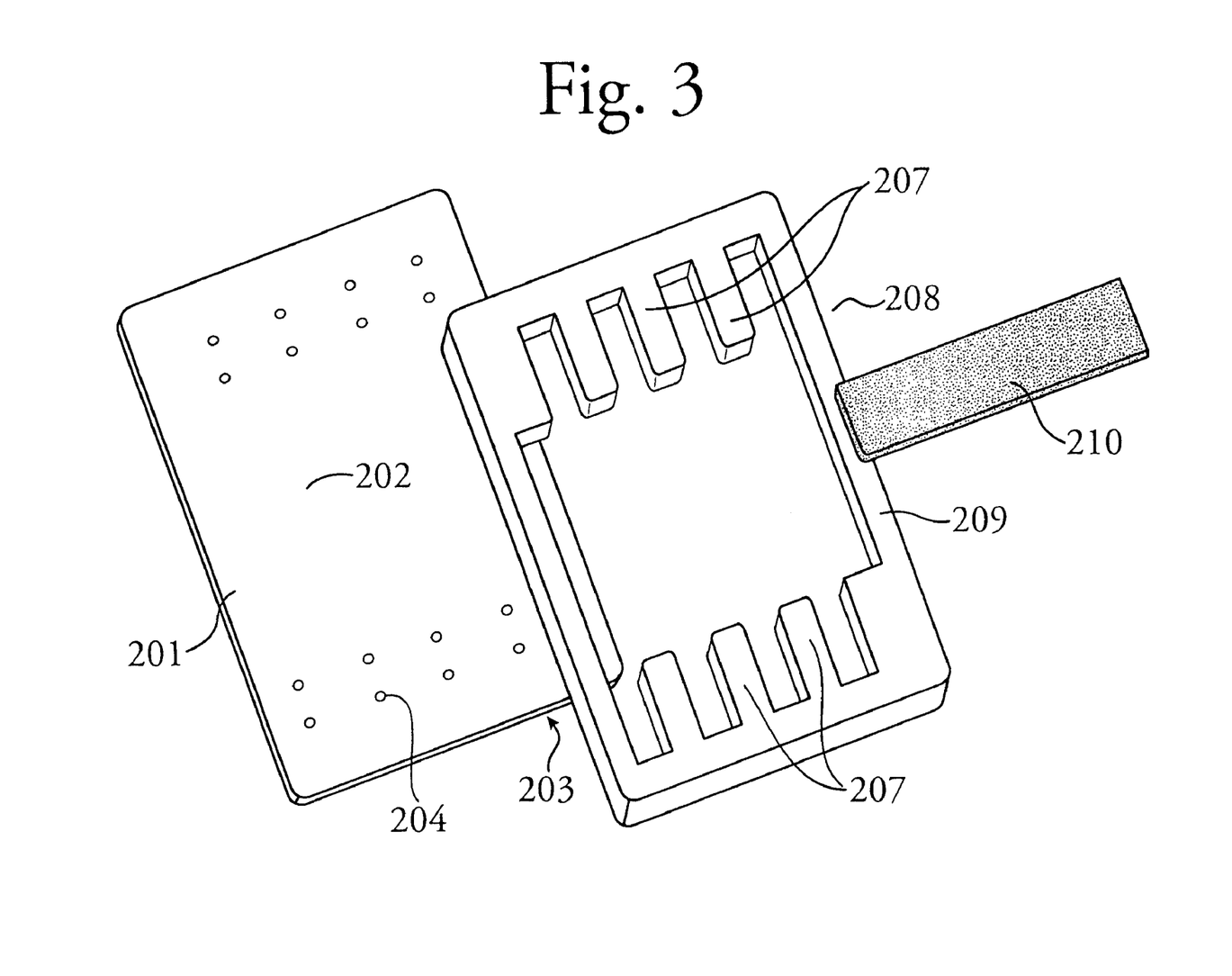
FIG. 3 is an exploded view of the embodiment of the adaptor plate shown in FIG. 2.
Figure 4:
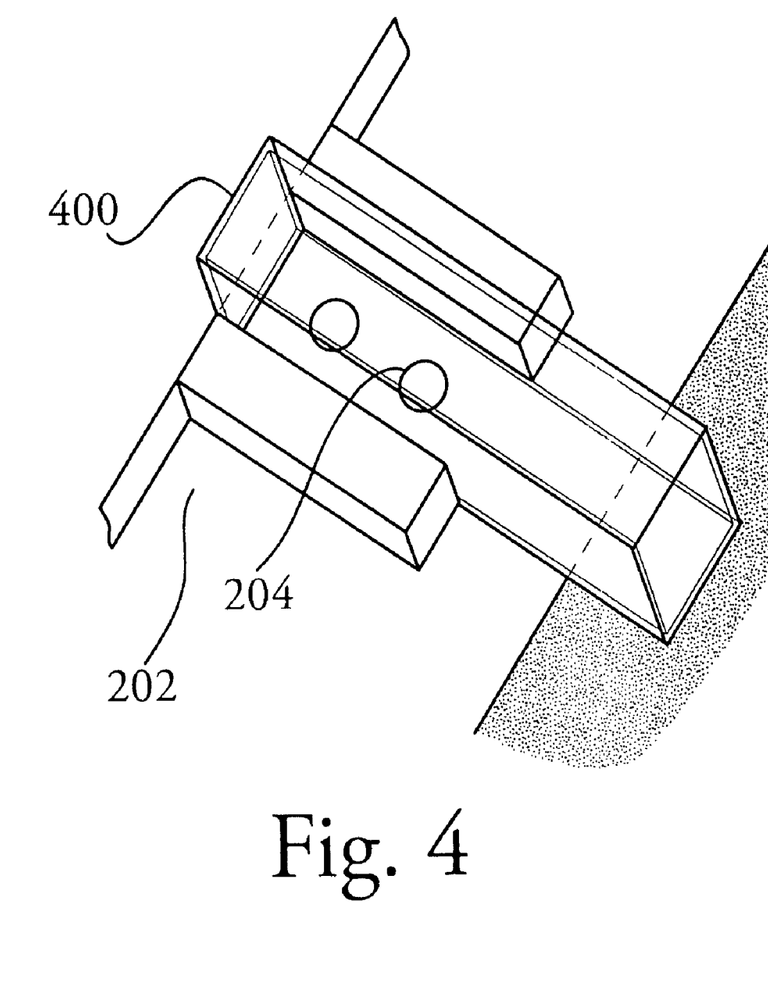
FIG. 4 is a close-up, cut-away view of the embodiment of the adaptor plate of the present invention as shown in FIG. 2, including a cuvette.

As shown in FIGS. 2, 3, and 4, one embodiment of the present invention is an adaptor plate 200 for use in a vertical light beam spectrophotometer 211 suitable for supporting a conventional rectangular cuvette 400 or cuvettes. Adaptor plate 200 includes a an opaque plate 201, forming a base or support for cuvettes. Opaque plate 201 may be constructed of metal, plastic, or any other opaque material known to one skilled in the art. For example, opaque plate 201 may be made of aluminum, steel, or a polymer.

The opaque plate 201 has a top face 202 with a generally planar surface, a bottom face 203 (not shown), and openings 204 for allowing the passage of light through the top face and the bottom face.

Figure 5:
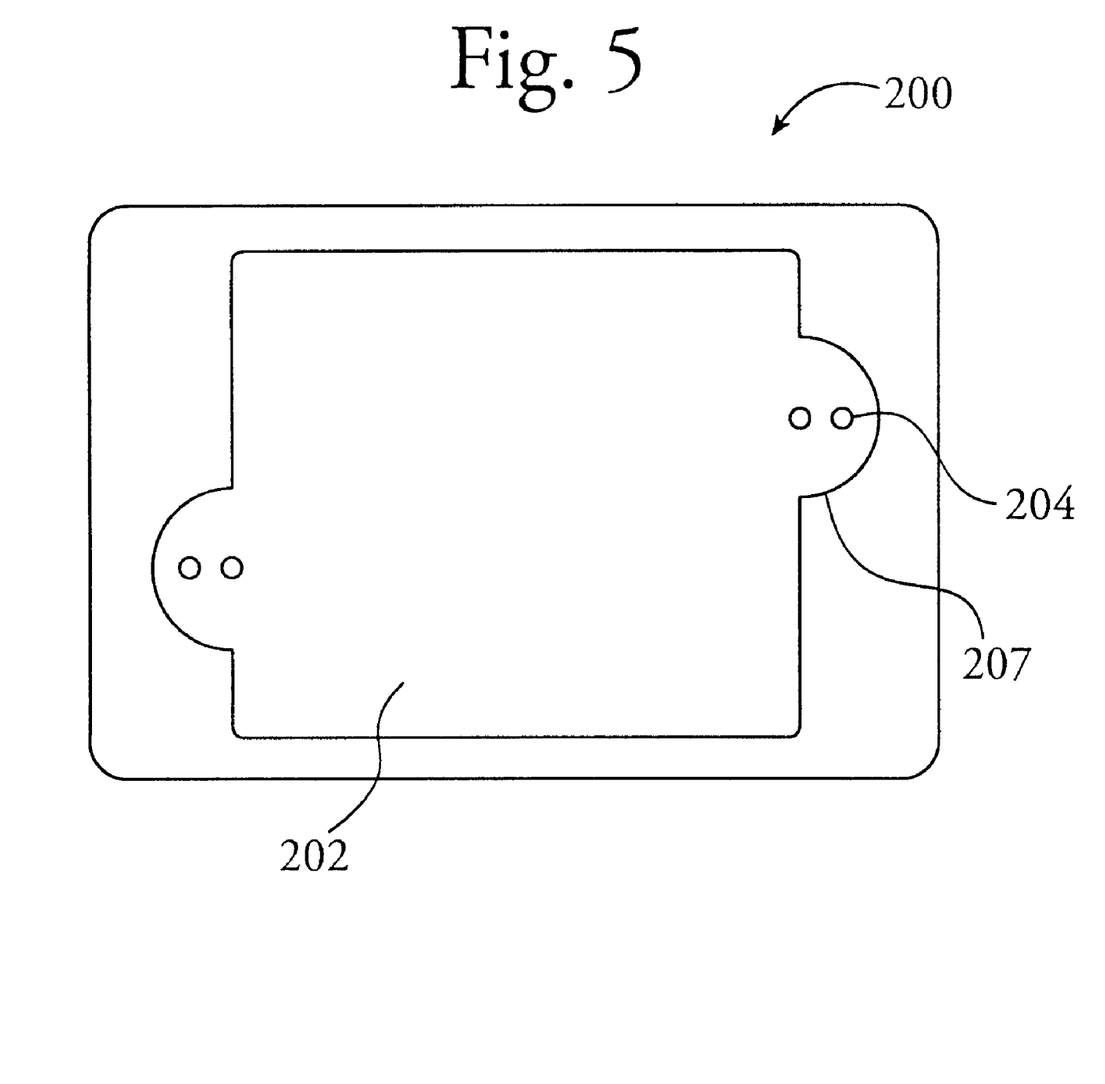
FIG. 5 a top view of a second embodiment of the adaptor plate of the present invention.
Figure 6:
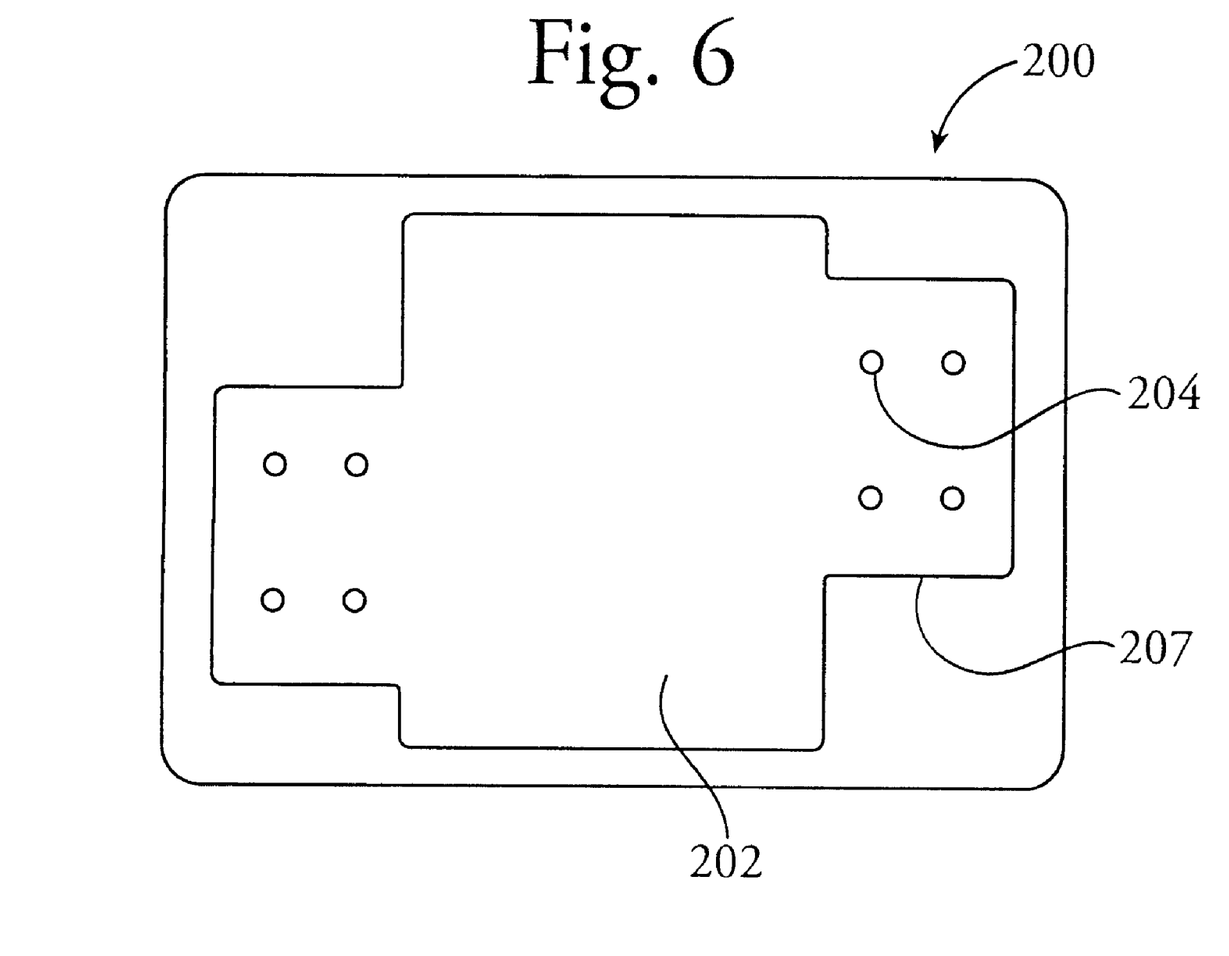
FIG. 6 is a top view of a third embodiment of the adaptor plate of the present invention.

The openings 204 for allowing the passage of light through the top face and the bottom face of opaque plate 201 may disposed on opaque plate 201 in any variety of patterns or configurations known in the art. For example, openings 204 may be disposed in a pattern substantially consistent with any suitable industry standard, such as ANSI SBS 1, 2, 3, or 4-2004, for analyzing rectangular cells. These standards are incorporated herein by reference. Alternatively, openings 204 may be configured to analyze cylindrical cells as shown in FIG. 5, or wide cells as shown in FIG. 6. As will be apparent to one skilled in the art, openings 204 may be disposed in any manner that allows light from to pass through opaque plate 201 and a cuvette containing a sample situated on top of opaque plate 201 to reach a detector.

Adaptor plate 200 may include just one or a number of openings 204 (as shown in FIG. 2). In one embodiment, openings 204 are disposed only in positions which will be aligned with the desired rectangular cuvettes. In another embodiment, the openings 204 are disposed only near the outer longitudinal 205 and/or latitudinal 206 edges of the opaque plate 201.

The adaptor plate 200 may further include aligning walls 207 for aligning cuvettes disposed on the opaque plate 201. Aligning walls 207 may be used to align or position a cuvette on opaque plate 201. When a cuvette 400 is disposed on the opaque plate 201 between two of the aligning walls 207, the cuvette 400 is generally aligned in a position over at least one of the openings 204.

The distance from a cuvette-facing surface of a first aligning wall 207 to an adjacent cuvette-facing surface of a second aligning wall 207 may be slightly greater than the width of the cuvettes intended to be used with the adaptor plate. It is contemplated that cuvettes can be retained by the aligning walls 207 on adaptor plate 200 during analysis to restrict the cuvettes' movement. Any number aligning walls 207 can be disposed between multiple cuvettes.

Each aligning wall 207 may be disposed on adaptor plate 200 individually. Alternatively, each aligning wall may be a surface of top face 202 situated above or below the top face 200's generally planar surface (e.g., in the form of ridges, rises, or depressions). Aligning walls 207 may further take any shape or be any length sufficient to: (a) align a cuvette over an opening 204; and/or (b) restrict the movement of a cuvette on the opaque plate 201 during handling or analysis.

Alternatively, aligning walls 207 may be formed as part of a top plate 208, (or, e.g., a layer or sheet), as shown in FIGS. 2 and 3. In the embodiment shown in FIGS. 2 and 3, top plate 208 includes multiple aligning walls 207 represented as "fingers" or "teeth" extending from a common border 209. Top plate 208 may fabricated out of any suitable material known in the art, e.g., a polymer, polypropylene, etc. Top plate 208 may be aligned over or connected to opaque plate 201 by any means known in the art, e.g., glue.

The top face 202 of opaque plate 201 may further include a raised element 210 for propping an end of a cuvette in a direction vertical to the planar surface of the top face 202. As shown in FIGS. 2-4, this raised element 210 for propping an end of a cuvette may be, for example, disposed near the mid-point of the longitudinal axis on the opaque plate 201, and in a direction generally parallel to the latitudinal edge 206 of the opaque plate 201. However, it will be apparent to one skilled in the art that the raised element 210 may be disposed any place on the top face 202 such that at least one end of a cuvette can be positioned on the raised element 210 to achieve a vertical clearance from the planar surface of the top face 202 relative to the opposite end of the cuvette. It should also be apparent to one skilled in the art that the raised element 210 may be disposed in any position on top lace 202 to prop one end of a cuvette. e.g., the upper portion of a cuvette, such that the one end of the cuvette achieves a vertical tilt. The vertical tilt of the cuvette may be desirable to direct any gas bubbles toward the vertically titled end and away from a sample aligned over an opening 204.

Raised element 210 may be constructed of any material sufficient for the purpose of propping an end of a cuvette in a direction vertical to the planar surface of top face 202. For example, raised element 210 may be tape, as shown in FIGS. 2-4, disposed on top of top face 202. Alternatively, raised element 210 may be an integral, raised portion of the surface of top face 202. Additionally, raised element 210 may be any material operable to tilt up and, optionally, removably affix a cuvette. It should further be apparent that the top face 202 can include two or more separate raised elements 210 for propping multiple cuvettes. For example, top face 202 may include a separately raised element 210 for each of multiple cuvettes.

Figure 7:
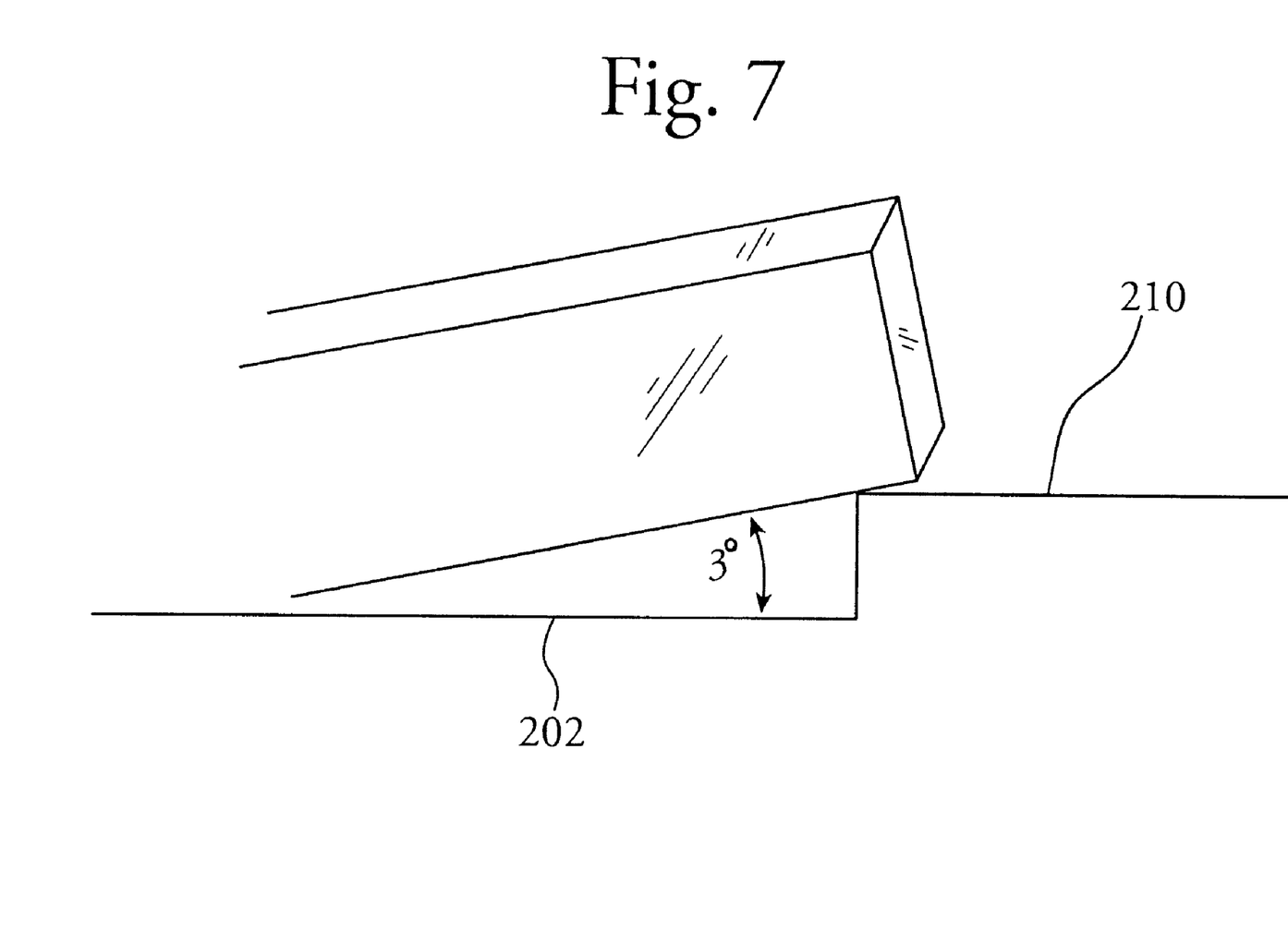
FIG. 7 is a side view of a cuvette disposed on a raised element of one embodiment of the adaptor plate of the present invention, illustrating an exemplary degree of vertical clearance.

In one embodiment, the height of the raised element 210 is sufficient to achieve a tilt of the cuvette as discussed above. For example, the raised element 210 may rise to a height of about 0.5 to 2 mm above the planar surface of the top face 202. Similarly, the raised element 210 has a height sufficient to prop the end of a cuvette in a direction between 1 and 4 degrees vertical to the generally planar surface of the top face 202, as shown in FIG. 7. The upper limit on the degree of tilt is constrained by the geometry of the sample area in the vertical light beam spectrometer being used.

The adaptor plate 100 may constructed in various ways known to those skilled in the art. In one embodiment, opaque plate 201 (having top face 202, bottom face 203, and openings 204) and raised element 210 are a one-piece, unitary construction. Such a unitary construction may be made by, for example, molded plastic or other method. In another embodiment, opaque plate 201 (having top face 202, bottom face 203, and openings 204) and raised element 210 are two separate pieces aligned and/or joined together as described above. In a further embodiment, opaque plate 201 (having top face 202, bottom face 203, and openings 204), raised element 210, and aligning walls 207 are made of a one-piece, unitary construction. In an even further embodiment, opaque plate 201, raised element 210, and aligning walls 207 are three separate pieces aligned and/or joined together. Other combinations are also contemplated. For example, opaque plate 201 and raised element 210 may be a one-piece, unitary construction used in conjunction with to a separate top plate including aligning walls 207. Alternatively, opaque plate 201 and aligning walls 207 may be a one-piece, unitary construction used in conjunction with a separate raised element 210.

In a further embodiment, a method for using the adaptor plate described above in a vertical light beam spectrophotometer is contemplated. A user may provide an adaptor plate having any of the configurations discussed above. For example, the adaptor plate may have: a generally rectangular opaque plate including one or more openings for allowing the passage of light through the opaque plate; a raised element for propping one end of a cuvette in a vertical direction relative to the opposite end of the cuvette; and aligning walls for aligning or restricting the movement of a cuvette. The user may align a cuvette having upper and lower portions and a sample to be measured between two aligning walls on the adaptor plate. In particular, the user may further align the cuvette over one or more of the openings for allowing the passage of light through the opaque plate, such that the sample to be measured is disposed in a light path through the opaque plate. The user may then position one end of the cuvette on or in contact with the raised element to prop the end of the cuvette in a vertical direction relative to the opposite end of the cuvette. In one example, the vertical clearance between the end of the cuvette and the generally planar surface of the opaque plate is about 3 degrees, plus or minus one degree. The user may then operate the vertical light beam spectrophotometer to transmit light through the cuvette, sample, and opening in the opaque plate to obtain a reading with respect to the sample. The technique described above may be used in, for example, absorption spectroscopy and fluorescence spectroscopy.

In an even further embodiment, a method for validating a vertical light beam spectrophotometer using the adaptor plate described above is contemplated. A user may provide a cuvette having a reference sample (i.e., a blank, or a cuvette containing a reference sample as discussed above) with a first end and a second end opposite the first end on an adaptor plate having: (a) a top face, (b) a bottom face, and (c) one or more openings for passage of light through the plate. The first end of the cuvette may be propped in a vertical direction relative to the opposite end of the cuvette. The user may also align the cuvette over the one or more openings, such that light passes through the cuvette. Using the vertical light beam spectrophotometer, the user then obtains a reading or measurement. The user then determines whether the vertical light beam spectrophotometer is performing within acceptable tolerance limits by, for example, comparing the reading with the reference sample's known measurement value. Typically, if the reading does not deviate from the reference sample's known measurement value (or does not deviate outside of an acceptable percentage or tolerance), the user determines that the vertical light beam spectrophotometer is performing within acceptable tolerance limits. It the reading significantly deviates from the reference sample's known measurement (i.e., beyond or outside of the acceptable tolerance limit), the user determines that the vertical light beam spectrophotometer is not performing within acceptable tolerance limits.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention. Therefore, it is intended that the invention not be limited to the particular embodiments disclosed as the best mode contemplated for carrying out this invention, but that the invention will include all embodiments falling within the scope and spirit of the appended claims.

The invention claimed is:

1. An apparatus for use with cuvettes in a vertical light beam spectrophotometer comprising:
   a plate having a top face, a bottom face, and one or more openings for passage of light through the plate;
   wherein at least a portion of the top face is configured such that an end of at least one cuvette aligned over one or more of the openings in the top face is propped in a vertical direction relative to the opposite end of the cuvette.

2. The apparatus of claim 1 wherein the plate is opaque.

3. The apparatus of claim 1 wherein at least a portion of the top face is an inclined surface.

4. The apparatus of claim 1, wherein the one or more openings for allowing the passage of light through the plate are disposed in a pattern substantially consistent with any of ANSI SBS 1, 2, 3, 4-2004 standards for vertical light beam spectrophotometers.

5. The apparatus of claim 1, wherein the plate further includes a longitudinal edge and a latitudinal edge.

6. The apparatus of claim 1, further including a top plate joinable to the top face of the plate or claim 1, wherein the top plate has one or more openings alignable with the one or more openings of the plate of claim 1 for passage of light through the top plate and the plate of claim 1, further wherein the top plate has portions configured to align at least one cuvette over the one or more openings of the plate of claim 1.

7. The apparatus of claim 1, further comprising one or more aligning walls for aligning one or more surfaces of a cuvette disposed on the top face, such that the aligning walls align at least one cuvette in a position over at least one of the openings for passage of light through the plate.

8. The apparatus of claim 1 wherein the top face includes a raised element for propping an end of at least one cuvette in a vertical direction relative to the opposite end of the cuvette.

9. The apparatus of claim 7, further comprising at least two aligning walls, wherein the distance from an outer surface of a first aligning wall to an outer surface of a second aligning wall is approximately equal to or greater than the width of the cuvette.

10. The apparatus of claim 9, wherein the top face, bottom face, a raised element for propping at least one cuvette in a vertical direction relative to the opposite end of the cuvette, and two or more aligning walls are made of a one-piece construction.

11. The apparatus of claim 8 wherein the raised element is removable.

12. The apparatus of claim 8, wherein said raised element for propping the end of the cuvette is disposed on the plate in a direction generally parallel to the latitudinal edge of the plate.

13. The apparatus of claim 8, wherein the top face includes two or more raised elements for propping ends of two or more cuvettes.

14. The apparatus of claim 8, wherein the top face has a generally planar surface and the raised element has a height of about 0.5 to 2 mm above the generally planar surface of the top face.

15. A apparatus for use with cuvettes in a vertical light beam spectrophotometer comprising:
a plate having a top face, a bottom face, and one or more openings for passage of light through the plate;
wherein at least a portion of the top face is configured such that a first end of at least one cuvette is alignable over one or more of the openings in the top face by one or more aligning walls and a second end of the at least one cuvette is propped in a vertical direction relative to the first end of the cuvette by a raised element.

16. An apparatus for use with cuvettes in a vertical light beam spectrophotometer comprising:
a generally rectangular plate having one or more openings for passage of light through the plate;
a means for propping an end of at least one cuvette in a vertical direction relative to the opposite end of the cuvette; and
a means for aligning the cuvette over the one or more openings.

17. The apparatus of claim 16 wherein the generally rectangular plate, the propping means, and the aligning means, are made of a one-piece, unitary construction.

18. The apparatus of claim 16, wherein the propping means props end of the cuvette a vertical distance between 0.5 to 2 mm relative to a generally planar surface of a top face of the generally rectangular plate.

19. The apparatus of claim 16, wherein the propping means is operable to prop the end of the cuvette 1 to 4 degrees relative to the opposite end of the cuvette.

20. The apparatus of claim 19, wherein the propping means is operable to prop the cuvette about 3 degrees.

21. A method for using an adaptor plate in a vertical light beam spectrophotometer, said method comprising the steps of:
providing at least one cuvette with a first end and a second end opposite the first end;
providing an adaptor plate having: (a) a top face, (b) a bottom face, and (c) one or more openings for passage of light through the plate, wherein at least a portion of the top face is configured such that the first end of at least one cuvette is propped in a vertical direction relative to the opposite end of the cuvette;
aligning the cuvette over the one or more openings, such that light passes through the cuvette; and
using the vertical spectrophotometer to obtain a reading for a sample in the cuvette.

22. A method of validating a vertical light beam spectrophotometer, said method comprising the steps of:
providing at least one cuvette with a first end and a second end opposite the first end and containing a reference sample;
providing an adaptor plate having: (a) a top face, (b) a bottom face, and (c) one or more openings for passage of light through the plate, wherein at least a portion of the top face is configured such that the first end of at least one cuvette is propped in a vertical direction relative to the opposite end of the cuvette;
aligning the cuvette over the one or more openings, such that light passes through the cuvette;
operating the vertical light beam spectrophotometer to obtain a reading for the reference sample; and
determining whether the vertical light beam spectrometer is performing within acceptable tolerance limits by comparing the reading with the reference sample's known measurement value.

23. The method of claim 22, wherein the step of determining whether the vertical light beam spectrometer is performing within acceptable tolerance limits by comparing the reading with the reference sample's known measurement value further comprises the step of determining that the vertical spectrophotometer is not performing within acceptable tolerance limits.

24. The method of claim 22 wherein the plate is opaque.

25. The method of claim 22 wherein at least a portion of the top face is an inclined surface.

26. The method of claim 22 wherein the top face includes a raised element for propping at least one cuvette in a vertical direction relative to the opposite end of the cuvette.

27. The method of claim 26 wherein the raised element is removable.

28. A vertical light beam spectrophotometer system, comprising:
a vertical light beam spectrophotometer; and
an adaptor plate for use with cuvettes in the vertical light beam spectrophotometer, wherein the adaptor plate has a top face, a bottom face, and one or more openings for passage of light from the vertical light beam spectrometer vertically through the plate; and wherein at least a portion of the top lace is configured such that an end of at least one cuvette aligned over one or more of the openings in the top face is propped in a vertical direction relative to the opposite end of the cuvette.

* * * * *